(12) United States Patent
Nichols et al.

(10) Patent No.: US 8,383,649 B2
(45) Date of Patent: Feb. 26, 2013

(54) CRYSTALLINE FORMS OF NALTREXONE METHOBROMIDE

(75) Inventors: Gary A. Nichols, Wildwood, MO (US); Robert E. Halvachs, Belleville, IL (US); Gary L. Cantrell, Troy, IL (US); Kevin R. Roesch, O'Fallon, IL (US); Joseph P. Haar, Jr., Edwardsville, IL (US)

(73) Assignee: Mallinckrodt LLC, Hazelwood, MO (US)

( * ) Notice: Subject to any disclaimer, the term of this patent is extended or adjusted under 35 U.S.C. 154(b) by 473 days.

(21) Appl. No.: 12/668,218

(22) PCT Filed: Jun. 25, 2008

(86) PCT No.: PCT/US2008/068103
§ 371 (c)(1),
(2), (4) Date: Jan. 8, 2010

(87) PCT Pub. No.: WO2009/009292
PCT Pub. Date: Jan. 15, 2009

(65) Prior Publication Data
US 2010/0324078 A1    Dec. 23, 2010

Related U.S. Application Data

(60) Provisional application No. 60/949,096, filed on Jul. 11, 2007.

(51) Int. Cl.
*A01N 43/40* (2006.01)
*A01N 43/02* (2006.01)
*A01N 43/08* (2006.01)
*A61K 31/445* (2006.01)
*A61K 31/335* (2006.01)
*A61K 31/34* (2006.01)

(52) U.S. Cl. ........ 514/315; 514/317; 514/449; 514/461; 514/468

(58) Field of Classification Search .................. 514/183, 514/315, 317, 449, 461, 468
See application file for complete search history.

(56) References Cited

U.S. PATENT DOCUMENTS

| | | |
|---|---|---|
| 4,176,186 A | 11/1979 | Goldberg et al. |
| 6,608,075 B2 | 8/2003 | Foss et al. |
| 2007/0265293 A1 | 11/2007 | Boyd et al. |
| 2008/0214817 A1 | 9/2008 | Dlubala |
| 2010/0305323 A1* | 12/2010 | Smolenskaya et al. ......... 546/45 |

FOREIGN PATENT DOCUMENTS

| | | |
|---|---|---|
| WO | WO 2004/043964 | 5/2004 |
| WO | WO 2004/091623 | 10/2004 |
| WO | WO 2004/108084 | 12/2004 |
| WO | WO 2006/127899 | 11/2006 |
| WO | WO 2008/109156 | 9/2008 |

* cited by examiner

*Primary Examiner* — Yong Chong

(57) ABSTRACT

The present invention relates to novel crystalline forms of naltrexone methobromide including hydrated and solvated forms. The invention also describes methods of preparing the various crystalline forms. The present invention also relates to pharmaceutical compositions containing crystalline forms of naltrexone methobromide, as well as methods of treating or preventing opioid induced side effects by administering the pharmaceutical compositions.

18 Claims, 5 Drawing Sheets

CRYSTALLINE FORMS OF NALTREXONE METHOBROMIDE

CROSS REFERENCE TO RELATED APPLICATIONS

This application is a national stage application of PCT/US2008/068103, filed Jun. 25, 2008, which claims the benefit of U.S. Provisional Application No. 60/949,096 filed Jul. 11 2007.

BACKGROUND OF THE INVENTION

1. Field of the Invention

The present invention relates to novel crystalline and amorphous forms of naltrexone methobromide. The invention also encompasses related processes, compositions, and methods.

2. Background of the Invention

Naltrexone methobromide is an opioid antagonist. The compound and methods for the synthesis of naltrexone methobromide are described in U.S. Pat. No. 4,176,186 and WO 2004/043964. Naltrexone methobromide (CAS: 73232-52-7) has the molecular formula $C_{21}H_{26}BrNO_4$ and the following structural formula:

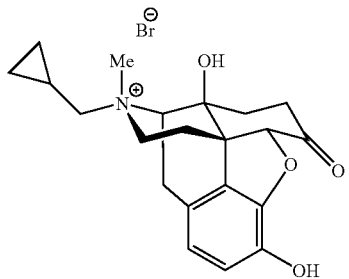

There is a need for new crystalline forms of naltrexone methobromide. The discovery of new crystalline forms of a pharmaceutical compound provides an opportunity to improve the performance characteristics of a pharmaceutical product. It enlarges the repertoire of materials that a formulation scientist has available for designing, for example, a pharmaceutical dosage form of a drug with a targeted release profile or other desirable characteristic.

WO 2004/108084 discloses polymorph forms of naltrexone base, however, naltrexone base and naltrexone methobromide are different molecular species and therefore do not possess the same solid-state properties.

All documents cited herein, including the foregoing, are incorporated by reference in their entireties for all purposes.

SUMMARY OF THE INVENTION

The present invention is directed to crystalline and amorphous forms of naltrexone methobromide, as well as mixtures thereof.

A further aspect of the present invention is directed to methods for preparing crystalline and amorphous forms of naltrexone methobromide.

The present invention further pertains to the use of these crystalline and amorphous forms of naltrexone methobromide in the treatment or prevention of opioid induced side effects, and to pharmaceutical formulations containing them.

Other novel features and advantages of the present invention will become more apparent to those skilled in the art upon examination of the following or upon learning by practice of the invention.

DETAILED DESCRIPTION OF THE INVENTION

Figure 1:
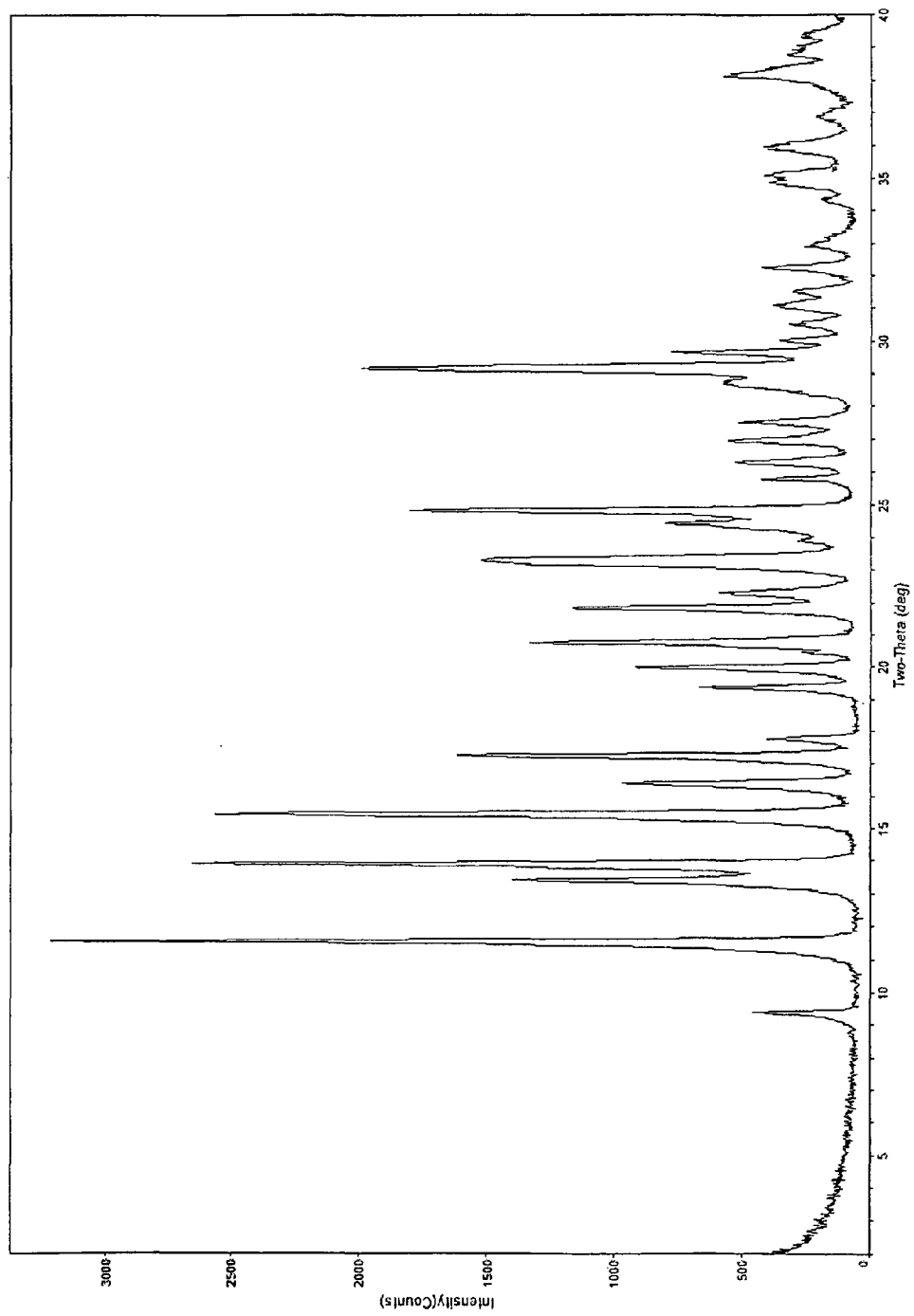
FIG. 1 shows the powder X-ray diffraction (pXRD) pattern for a crystalline form of naltrexone methobromide—Form I.

The present invention describes several novel crystalline forms and an amorphous form of naltrexone methobromide and methods of making crystalline and amorphous forms of naltrexone methobromide.

Crystalline forms of naltrexone methobromide are made or transformed under different environmental conditions, such as exposure to heat or light, mechanical handling, interaction with excipients, or when placed in contact with water, organic solvents, mixtures of solvents, or vapor of solvents. Certain crystalline forms of naltrexone methobromide may be more stable in a given environmental condition or selected solvent system because each crystalline form may exhibit distinct physical and chemical properties. These properties include particle size, surface area, shape, flow characteristics, solubility, melting point, degree of hydration or solvation, and caking tendency. These properties may affect chemical processing, material handling, compatibility with excipients, segregation in a blend, dissolution rate of naltrexone methobromide in aqueous media, and stability of the final dosage form. Adverse effects may cause loss of production efficiency (time and cost), product quality and instability. Thus it is desirable to use a crystalline form of naltrexone methobromide with improved characteristics over other forms.

The methods used to produce novel crystalline and amorphous forms from naltrexone methobromide are set forth below.

Preparation of Crystalline and Amorphous Forms of Naltrexone Methobromide

Crystalline and amorphous forms of naltrexone methobromide may be prepared by the crystallization, precipitation, or slurry of naltrexone methobromide anhydrous (Mallinckrodt Inc.) out of a variety of solvent systems, including but not limited to methanol, isopropanol, ethanol, water, n-butanol, acetone, glacial acetic acid, hydrobromic acid, ethyl acetate, methylene chloride, chloroform, acetonitrile, tetrahydrofuran (THF), hexane, toluene, dimethylsulfoxide (DMSO), ethyl ether, N,N-dimethylformamide or N,N-dimethylacetamide and mixtures thereof. In one embodiment, when two solvents are employed in the solvent system, the solvents may be present in a ratio from about 1:1 to about 1:100. In another embodiment, two solvent systems may be used: a first solvent system, in which naltrexone methobromide is particularly soluble, and a second solvent system, in which naltrexone methobromide is less soluble and typically more volatile than in the first solvent system.

Various methods of crystallization include but are not limited to slow evaporation, rapid evaporation, "hot" preparation, and slow diffusion. With these methods, the solvent may be evaporated off the solid naltrexone methobromide or solid naltrexone methobromide may be filtered from the residual solvent and dried. In one embodiment, the solid naltrexone methobromide is filtered using a fritted disc funnel and dried in a desiccator under vacuum.

In one embodiment, for slow evaporation experiments, each solvent system is saturated/near saturated with naltrexone methobromide in a small vial and set aside at room temperature and pressure to evaporate the solvent for an amount of time sufficient to induce crystallization of at least one crystalline form of naltrexone methobromide. In one embodiment, the amount of time sufficient to induce crystallization is from about 1 day to about 60 days. Following crystal growth, the solid material may be filtered from the residual solvent using a fritted disc funnel and dried in a desiccator under vacuum.

In another embodiment, rapid evaporation experiments are performed by saturating\near saturating a solvent system with naltrexone methobromide and then quickly roto-evaporating off the solvent.

In yet another embodiment, described as "hot" preparation, an aliquot of each solvent system is heated to boiling/near boiling. Naltrexone methobromide is then added slowly until the solvent is saturated/near saturated. The solution is then cooled to induce crystallization of at least one crystalline form of naltrexone methobromide. In one embodiment, the solution is cooled at room temperature for an amount of time sufficient to induce crystallization. In another embodiment, the solution is cooled by placing the solution in an ice bath to induce crystallization. Following crystal growth, the solid material may be filtered from the residual solvent using a fritted disc funnel and dried in a desiccator under vacuum.

In yet another embodiment, slow diffusion experiments are performed by dissolving naltrexone methobromide in a first solvent system, in which the naltrexone methobromide is soluble, in a small vial and then placing the small vial in a sealed larger flask that contains a second solvent system, in which naltrexone methobromide is less soluble and is typically more volatile than the first solvent system. In one embodiment, the first solvent system is either ethanol or methanol and the second solvent system is ethyl acetate, hexane, chloroform, or ethyl ether. The flask is set aside for an amount of time sufficient to allow for vapor equilibration and crystallization of the naltrexone methobromide. Following crystal growth, the solid material may be filtered from the residual solvent using a fritted disc funnel and dried in a desiccator under vacuum.

For slurry preparations, a solvent system is saturated with naltrexone methobromide in a flask or similar container to which additional solid naltrexone methobromide is added. The resulting slurry is then stirred for an amount of time sufficient to convert a first crystalline form of naltrexone methobromide to a second crystalline form of naltrexone methobromide, using for example, a magnetic stir-bar. In a preferred embodiment, the slurry is stirred for preferably 10 to 20 days, more preferably, 13 to 17 days, most preferably 13, 15 or 17 days. The second crystalline form of naltrexone methobromide may then be filtered from the residual solvent, for example, with a fritted disc funnel.

Precipitation preparations may be completed by first dissolving naltrexone methobromide in a first solvent system in which naltrexone methobromide is particularly soluble and then adding a second solvent system, in which naltrexone methobromide is less soluble, slowly to precipitate the naltrexone methobromide from solution.

The prepared crystalline forms of naltrexone methobromide were subsequently characterized by powder X-ray diffraction ("pXRD") analysis, differential scanning calorimetry, and thermogravimetric analysis.

pXRD pXRD analysis was conducted using a Siemens D500 X-ray Diffractometer. All samples were unground, uniformly crushed with a spatula edge, and placed on a quartz, zero background holder. The following instrument parameters were utilized: Scan range: 2.0 to 40.0° 2θ, Step size: 0.02° 2θ, Scan time per step: 1.0 seconds, Radiation source: copper Kα (1.5406 Å), X-ray tube power: 40 kV/30 mA. Those skilled in the art of X-ray crystallography will appreciate that peak positions determined on different instruments may vary by as much as ±0.2 degrees.

Figure 2:
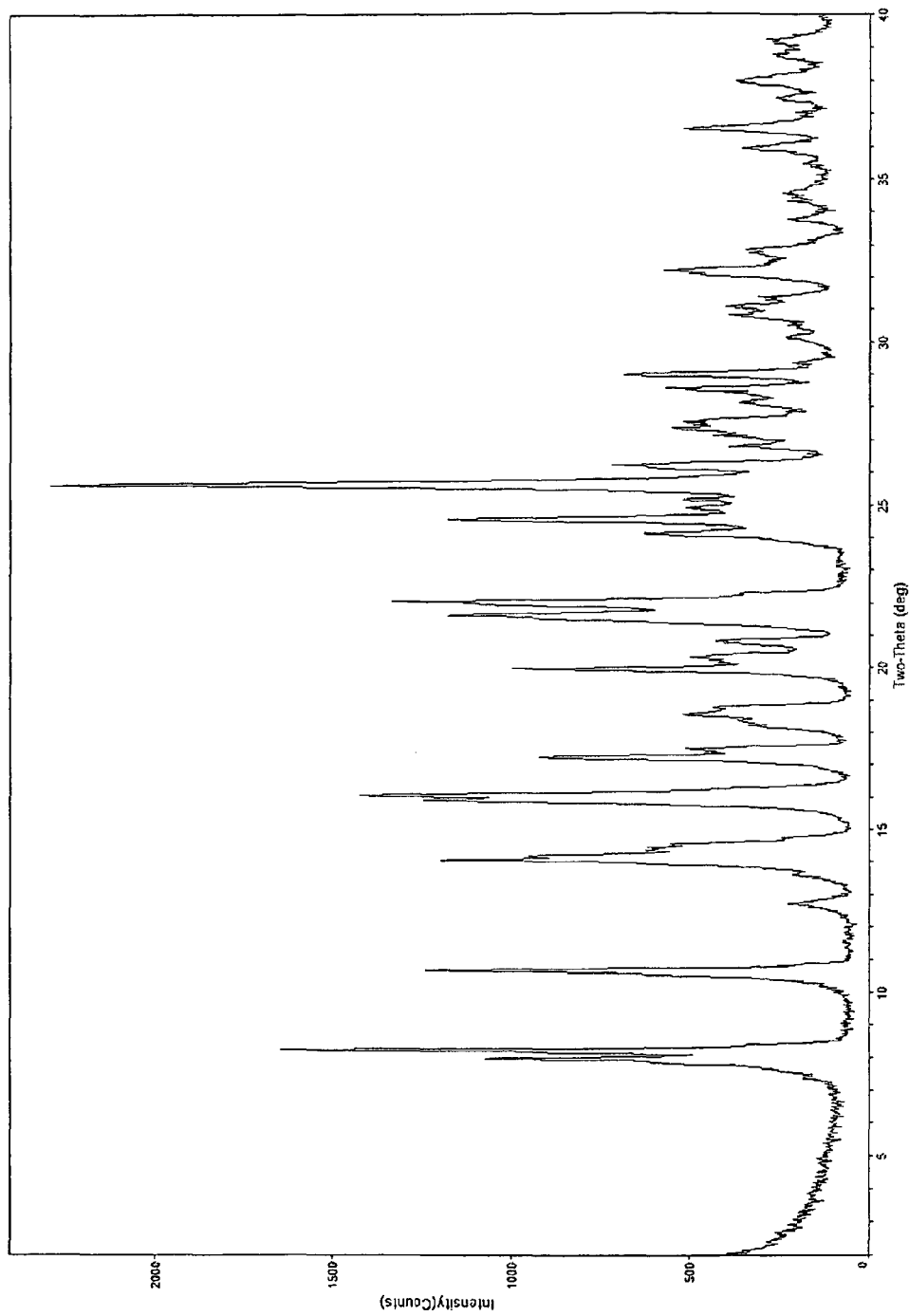
FIG. 2 shows the pXRD pattern for a crystalline form of naltrexone methobromide—Form II.
Figure 3:
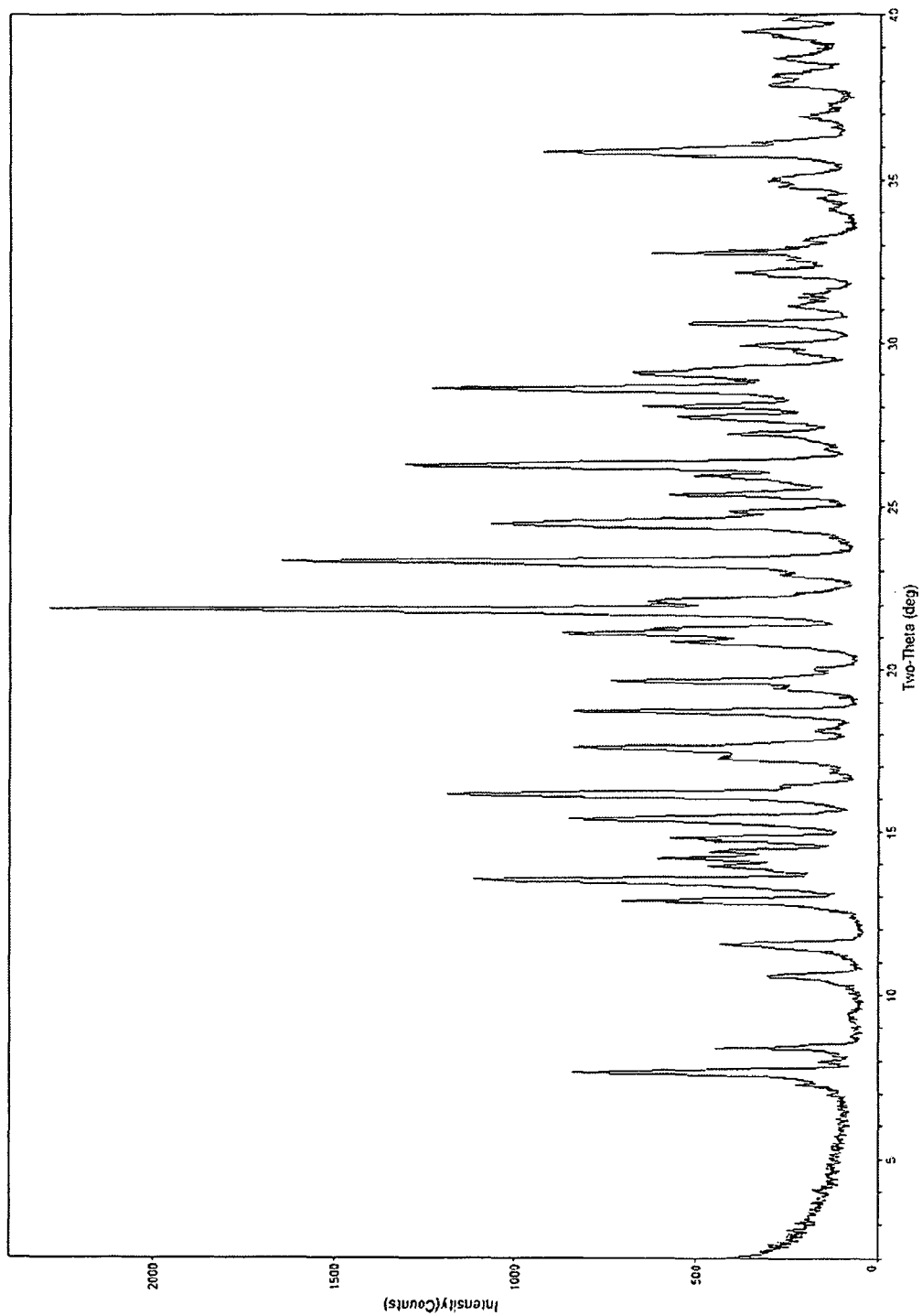
FIG. 3 shows the pXRD pattern for a crystalline form of naltrexone methobromide—Form III.

Each crystalline form of naltrexone methobromide exhibited a distinctly different pXRD pattern as set forth in FIGS. 1 to 3 and Table 1.

TABLE 1

Crystalline Naltrexone Methobromide XRPD Peak (°2θ) and Relative Intensities

| Form I | | Form II | | Form III | |
| --- | --- | --- | --- | --- | --- |
| °2θ | Ht I % | °2θ | Ht I % | °2θ | Ht I % |
| 9.4 | 12.6 | 8.0 | 41.8 | 7.7 | 35.0 |
| 11.6 | 100.0 | 8.3 | 74.2 | 8.4 | 17.9 |
| 13.5 | 42.2 | 10.7 | 55.0 | 10.6 | 11.2 |
| 14.0 | 81.2 | 12.8 | 7.9 | 11.6 | 17.7 |
| 15.5 | 78.2 | 14.1 | 52.9 | 12.9 | 30.5 |
| 16.4 | 27.4 | 14.5 | 25.0 | 13.6 | 45.2 |
| 17.3 | 48.6 | 16.0 | 61.0 | 14.0 | 14.7 |
| 17.8 | 10.7 | 17.3 | 39.5 | 14.2 | 21.0 |
| 19.4 | 18.6 | 17.5 | 20.3 | 14.4 | 13.0 |
| 20.0 | 25.8 | 18.2 | 12.1 | 14.8 | 19.0 |
| 20.8 | 39.1 | 18.6 | 18.2 | 15.4 | 33.8 |
| 21.9 | 34.0 | 20.0 | 43.6 | 16.2 | 50.4 |
| 22.3 | 15.8 | 20.4 | 18.8 | 16.4 | 8.2 |
| 23.3 | 44.0 | 20.8 | 12.0 | 17.3 | 15.9 |
| 24.5 | 22.6 | 21.6 | 50.2 | 17.6 | 34.5 |
| 24.8 | 54.5 | 22.1 | 57.9 | 18.7 | 34.8 |
| 25.8 | 10.7 | 24.2 | 25.2 | 19.4 | 8.5 |
| 26.3 | 13.5 | 24.6 | 51.3 | 19.7 | 30.6 |
| 27.0 | 14.3 | 25.6 | 100.0 | 20.9 | 23.1 |
| 27.6 | 13.2 | 26.2 | 26.4 | 21.2 | 36.9 |
| 28.7 | 15.3 | 26.8 | 10.6 | 21.9 | 100.0 |
| 289.2 | 58.7 | 27.6 | 15.1 | 22.1 | 24.0 |
| 29.7 | 19.9 | 28.2 | 7.3 | 22.9 | 8.5 |
| 30.6 | 5.8 | 28.6 | 18.4 | 23.3 | 72.3 |
| 31.1 | 8.1 | 29.0 | 23.4 | 24.5 | 44.4 |
| 31.5 | 6.3 | 30.9 | 12.4 | 24.9 | 13.3 |
| 32.3 | 10.5 | 31.4 | 7.8 | 25.4 | 19.1 |
| 33.0 | 5.3 | 32.2 | 19.9 | 25.9 | 17.9 |
| 34.9 | 8.7 | 32.9 | 10.7 | 26.3 | 54.1 |
| 35.2 | 8.8 | 33.8 | 5.5 | 27.2 | 12.0 |
| 36.0 | 9.4 | 34.6 | 6.0 | 27.8 | 14.6 |
| 38.2 | 15.3 | 36.0 | 9.4 | 28.1 | 18.5 |
| 38.8 | 5.2 | 36.6 | 17.3 | 28.6 | 48.0 |
| | | 37.5 | 5.3 | 29.1 | 25.4 |
| | | 38.0 | 10.4 | 29.9 | 12.5 |
| | | 38.8 | 5.4 | 30.6 | 19.3 |
| | | 39.3 | 7.0 | 32.2 | 13.1 |
| | | | | 32.8 | 24.9 |
| | | | | 35.1 | 8.2 |
| | | | | 35.9 | 37.6 |
| | | | | 36.2 | 9.4 |
| | | | | 37.9 | 8.7 |
| | | | | 38.2 | 7.7 |
| | | | | 39.5 | 10.7 |

A crystalline naltrexone methobromide form having at least four of the peaks indicated by an asterisk (+/−0.2 deg 2θ) within one form of Table 1 are preferred embodiments of the invention. More preferable is a form having at least eight of the peaks that are indicated by an asterisk (+/−0.2 deg 2θ). Even more preferable is a form having at least ten of the peaks that are indicated by an asterisk (+/−0.2 deg 2θ). Even more preferable is a form having all of the peaks that are indicated in Table 1 for that particular form (+/−0.2 deg 2θ).

An amorphous form was also observed which had no distinct peaks in the pXRD pattern.

DSC

A TA Instruments Q100-differential scanning calorimeter was used. The samples were weighed into a hermetic, aluminum pan and sealed with a pinhole lid. The samples were heated from 25° C. to at least 200° C. at a rate of 5° C. per minute (unless otherwise noted).

Figure 4:
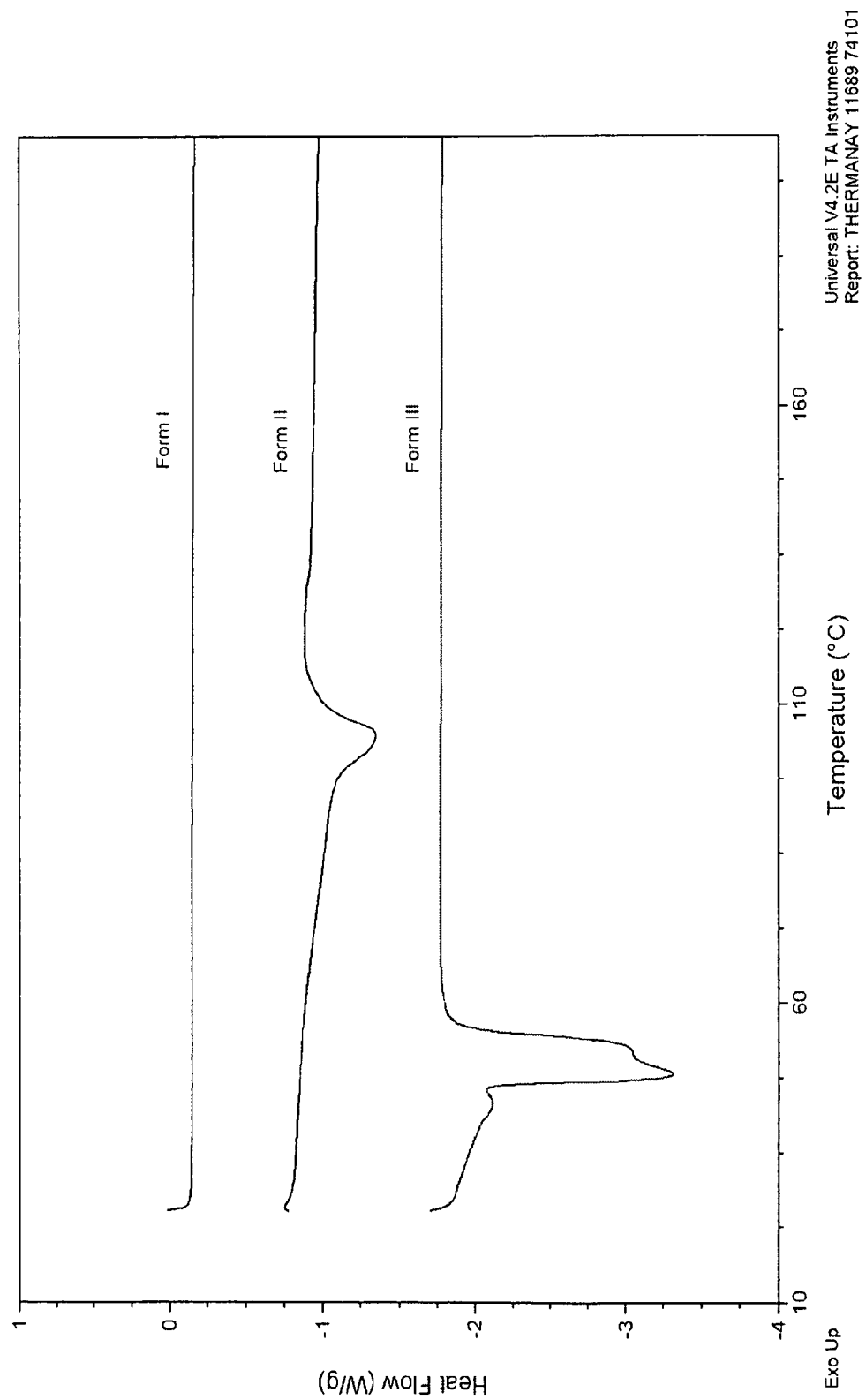
FIG. 4 shows the DSC trace for crystalline Forms I, II, and III of naltrexone methobromide.

The crystalline naltrexone methobromide Form I exhibits no significant transitions below 200° C. by DSC (FIG. 4). Naltrexone methobromide Form II exhibited a large endothermic transition from approximately 25° C. to 150° C. by DSC (FIG. 4). These transitions are associated with the loss of bound methanol and/or water. The DSC trace acquired for naltrexone methobromide Form III typically exhibit a large endothermic transition below 75° C. (FIG. 4).

TGA

TGA analysis was conducted using TA Instruments Q50 thermogravimetric analyzer. Each sample was weighed into an aluminum or ceramic sample pan and placed into the instrument. For TGA, samples were heated from room temperature to at least 200° C. at a rate of 5° C. per minute (unless otherwise indicated) with a nitrogen flow of 50 mL/min.

Figure 5:
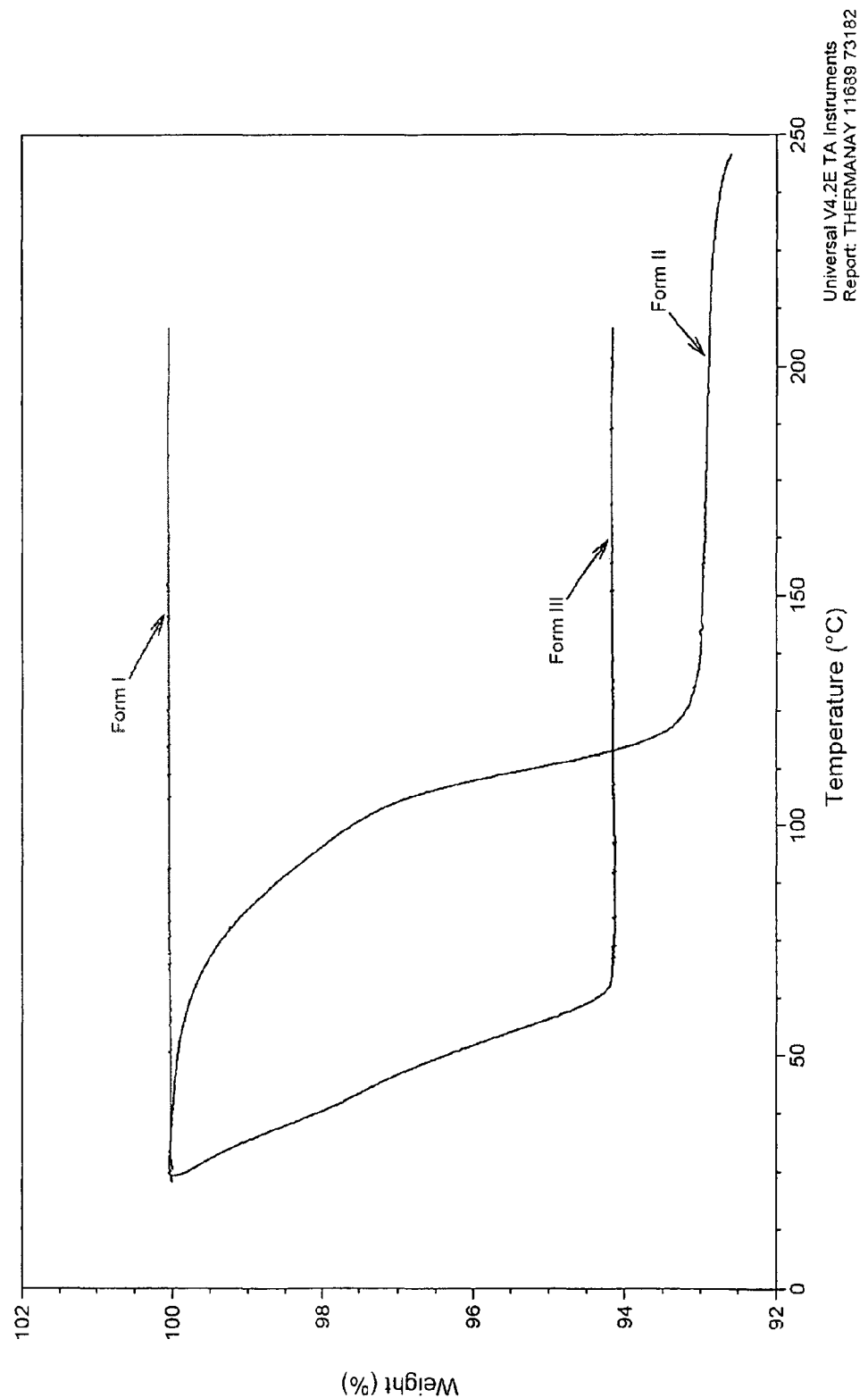
FIG. 5 shows the TGA trace for crystalline Forms I, II, and III of naltrexone methobromide.

The crystalline naltrexone methobromide Form I exhibits no significant loss of mass by TGA (FIG. 5). Naltrexone methobromide Form II typically exhibits a loss of mass, often in a step-wise fashion, anywhere from room temperature to almost 150° C. (FIG. 5). This loss of mass has been identified by FTIR as methanol, although some water was also observed to be lost over this temperature range. Naltrexone methobromide Form III typically exhibits a loss of mass below 75° C. This loss of mass was identified by FTIR as predominately associated with the loss of bound water.

The present invention describes novel forms obtained and characterized including naltrexone methobromide Forms II and III and amorphous naltrexone methobromide. Form II is a solvated crystalline form including from about 4.9% to 7.5% bound methanol. This form may contain bound methanol. Crystalline Form III was identified as a hydrated species. The water content of samples present as crystalline Form III was observed to vary from as low as about 3.5% to as high as about 6.0%.

The present invention also includes mixtures of the forms described herein. Thus, the invention includes, for example, naltrexone methobromide Form II alone or in combination with one or more of the other forms described herein. Such combinations can include compositions that have between 1 and 100% by weight of any particular form. Preferred amounts of one naltrexone methobromide form include at least about 10% by weight of the total crystalline product, preferably at least about 20%, at least about 30%, at least about 40%, at least about 50%, at least about 60%, at least about 70%, at least about 80%, or at least about 90% by weight of total crystallinity. The percentages represent the fraction of crystallinity as determined by relative peak intensity of characterizing peaks.

The crystalline and amorphous forms of the invention and the compositions containing them have the advantage that they are in a form which may provide for beneficial properties. For example, methanol is an excellent solvent to use in chemical processes, and therefore the methanol solvate of naltrexone methobromide (Form II) is likely isolated from processes that use this solvent.

In accordance with the present invention, these novel crystalline and amorphous forms of naltrexone methobromide may be prepared as pharmaceutical compositions that are particularly useful for the treatment of a patient afflicted with opioid induced side effects wherein such side effects may be treated or prevented by the administration of an effective amount of naltrexone methobromide of the present invention to a patient in need thereof. Such compositions can be manufactured utilizing techniques known in the art and comprise a therapeutically effective amount of at least one new crystalline form of naltrexone methobromide with pharmaceutically acceptable carriers, excipients and/or diluents that are known to those skilled in the art.

Naltrexone methobromide crystalline and amorphous forms may be administered to a person in a therapeutically effective amount, i.e. an amount effective to treat or prevent opioid-induced side effects including but not limited to constipation, immune suppression, inhibition of gastrointestinal motility, inhibition of gastric emptying, nausea, emesis, incomplete evacuation, bloating, abdominal distension, increased gastroesophageal reflux, hypotension, bradycardia, gastrointestinal dysfunction, pruritus, dysphoria, and urinary retention. The therapeutically effective amount of naltrexone methobromide crystalline form necessary to treat or prevent opioid-induced side effects is dependent upon the patient (size, age, health, and response, e.g.), the severity and extent of the side effects, the particular crystalline form employed, the method of administration, the bioavailability characteristic of the formulation administered, the dosing regimen, and other relevant circumstances. As used herein, the term "patient" refers to a warm blooded animal, including but not limited to humans, such as a mammal which is afflicted with a particular disease state.

Administration of pharmaceutical compositions including naltrexone methobromide crystalline or amorphous forms alone or in conjunction with other compounds can be local or systemic, or a combination of therapies. Systemic administration is preferred in some embodiments. Systemic administration can be via any method known in the art such as, for example, oral administration of lozenges, tablets, capsules, sub-lingual tablets, syrups, suspensions, granules, or other edible compositions; intravenous, intramuscular, or intradermal administration, e.g., by suspension, sterile injections, including depot versions; implants; parenteral administration of fluids and the like. In one embodiment, the novel naltrexone methobromide forms of this invention can be tabletted with conventional tablet bases such as lactose, sucrose, and cornstarch in combination with binders, such as microcrystalline cellulose, crospovidone, acacia, cornstarch, or gelatin, disintegrating agents such as potato starch or alginic acid, a lubricant such as hydroxypropyl methylcellulose, stearic acid or magnesium stearate, flavoring agents or coloring agents, such as yellow iron oxide and red iron oxide, and other excipients such as colloidal silicon dioxide, titanium dioxide, polyethylene glycol, and polysorbate 80. For parenteral administration the novel naltrexone methobromide forms may be dissolved in a physiologically acceptable pharmaceutical carrier and administered as either a solution or a suspension. Illustrative of suitable pharmaceutical carriers include water, saline, dextrose solutions, fructose solutions, ethanol, or oils of animal, vegetative, or synthetic origin. The pharmaceutical carrier may also contain preservatives and buffers as are known in the art.

For local administration, the novel naltrexone methobromide forms of the present invention may be topically applied to the skin or mucosa in association with a pharmaceutically acceptable carrier in which the naltrexone methobromide is dispersed or solubilized. Carriers may be aqueous compositions, lotions, creams, ointments, soaps, sustained release preparations such as patches and the like.

In one embodiment of the present invention, a naltrexone methobromide crystalline form is taken intraveneously as a sterile injection. Typical doses vary from about 0.01 mg/mL to about 100.0 mg/mL, and in preferred embodiments from about 0.1 mg/mL to about 100.0 mg/mL. In other embodiments, typical doses range from about 1.0 mg/mL to about 50.0 mg/mL. In another embodiment, a naltrexone methobromide crystalline form is administered orally as a tablet. Typical oral doses vary from about 0.1 mg to about 40.0 mg of naltrexone methobromide per kg body weight, and in preferred embodiments from about 0.1 mg to about 10 mg/kg body weight. In other embodiments, typical oral doses range from about 0.25 to about 80.0 mg/kg body weight, and in preferred embodiments from about 2.0 to about 20.0 mg/kg body weight. In still another embodiment, a naltrexone methobromide crystal form of the present invention is administered in a dose from about 0.25 to about 5.0 mg/kg body weight. Other preferred amounts and modes of administration are able to be determined by one skilled in the art using formulation technology known in the art, described for example in Remington's Pharmaceutical Sciences, latest edition, Mack Publishing Co.

In one embodiment, a dosing regimen includes administering intravenously to a patient in need 0.3 mg/kg of the naltrexone methobromide crystalline form up to four times per 24 hour period. Further, naltrexone methobromide crystalline forms of the present invention may be administered intravenously over a period of 1 to 7 days. Generally, oral doses of the naltrexone methobromide crystalline forms of the present invention will be from about 0.25 to about 5.0 mg/kg body weight per day. However, other dosing regimens may be used as the invention is not limited in this respect.

EXAMPLES

Naltrexone methobromide samples were prepared as described in Table 2 and the crystalline character of the naltrexone methobromide was demonstrated by pXRD analysis (FIGS. 2-3), DSC (FIG. 4) and TGA (FIG. 5).

TABLE 2

| Form | Description | Preparation |
| --- | --- | --- |
| II | Solvated - contains bound methanol | Obtained by slow evaporation from methanol or methanol/water/hydrobromic acid mixture or methylene chloride/methanol (5:1) mixture. Obtained by hot preparation of naltrexone methobromide in methanol or methanol/water mixture. |
| III | Hydrated - contains bound water (~3.5-6.0% by mass) | Obtained by slow evaporation from water or water/acetonitrile (2:5) mixture. Obtained by hot preparation from water or water/acetonitrile mixture. |
| amorphous | | Obtained by slow evaporation from water/acetonitrile (1:1) mixture and water/isopropanol (1:1) mixture. |

While the present invention has been described for what are presently considered the preferred embodiments, the invention is not so limited. To the contrary, the invention is intended to cover various modifications and equivalent arrangements included within the spirit and scope of the detailed description provided above.

The invention claimed is:

1. A crystalline form of naltrexone methobromide Form II characterized by an x-ray diffraction pattern having at least four characteristic peaks expressed in degrees 2θ (±0.2°) selected from 8.0, 8.3, 10.7, 14.1, 14.5, 16.0, 17.3, 17.5, 20.0, 21.6, 22.1, 24.2, 24.6, 25.6, and 26.2.

2. The crystalline form of naltrexone methobromide of claim 1 characterized by an x-ray diffraction pattern having at least eight characteristic peaks expressed in degrees 2θ (±0.2°) selected from 8.0, 8.3, 10.7, 14.1, 14.5, 16.0, 17.3, 17.5, 20.0, 21.6, 22.1, 24.2, 24.6, 25.6, and 26.2.

3. The crystalline form of naltrexone methobromide of claim 1 characterized by an x-ray diffraction pattern having at least ten characteristic peaks expressed in degrees 2θ (±0.2°) selected from 8.0, 8.3, 10.7, 14.1, 14.5, 16.0, 17.3, 17.5, 20.0, 21.6, 22.1, 24.2, 24.6, 25.6, and 26.2.

4. The crystalline form of naltrexone methobromide of claim 1 characterized by a powder x-ray diffraction pattern as shown in FIG. 2.

5. The crystalline form of naltrexone methobromide of claim 1 comprising bound methanol.

6. The crystalline form of naltrexone methobromide of claim 1 comprising from about 4.9% to 7.5% bound methanol.

7. The crystalline form of naltrexone methobromide of claim 1 characterized by a differential scanning calorimetry thermogram taken at a heating rate of 5° C./min, in a closed pan that exhibits a large endothermic transition at approximately 25° C. to 150° C.

8. The crystalline form of naltrexone methobromide of claim 1 characterized by no loss of mass prior to sublimation above 150° C.

9. A crystalline form of naltrexone methobromide Form III characterized by an x-ray diffraction pattern having at least eight characteristic peaks expressed in degrees 2θ (±0.2°) selected from 7.7, 12.9, 13.6, 15.4, 16.2, 17.6, 18.7, 19.7, 21.2, 21.9, 23.3, 24.5, 26.3, 28.6, and 35.9.

10. The crystalline form of naltrexone methobromide of claim 9 characterized by an x-ray diffraction pattern having at least eight characteristic peaks expressed in degrees 2θ (±0.2°) selected from 7.7, 12.9, 13.6, 15.4, 16.2, 17.6, 18.7, 19.7, 21.2, 21.9, 23.3, 24.5, 26.3, 28.6, and 35.9.

11. The crystalline form of naltrexone methobromide of claim 9 characterized by an x-ray diffraction pattern having at least ten characteristic peaks expressed in degrees 2θ (±0.2°) selected from 7.7, 12.9, 13.6, 15.4, 16.2, 17.6, 18.7, 19.7, 21.2, 21.9, 23.3, 24.5, 26.3, 28.6, and 35.9.

12. The crystalline form of naltrexone methobromide of claim 9 characterized by a powder x-ray diffraction pattern as shown in FIG. 3.

13. The crystalline form of naltrexone methobromide of claim 9 comprising bound water.

14. The crystalline form of naltrexone methobromide of claim 9 comprising from about 3.5% to about 6.0% water by mass.

15. The crystalline form of naltrexone methobromide of claim 9 characterized by a differential scanning calorimetry thermogram taken at a heating rate of 5° C./min. in a closed pan that exhibits a large endothermic transition below 75° C.

16. The crystalline form of naltrexone methobromide of claim 9 characterized by no loss of mass prior to sublimation above 75° C.

17. A pharmaceutical composition comprising a therapeutically-effective amount of the crystalline form of naltrexone methobromide Form II of claim 1.

18. A pharmaceutical composition comprising a therapeutically-effective amount of the crystalline form of naltrexone methobromide Form III of claim 9.

* * * * *